(12) United States Patent
Dexter et al.

(10) Patent No.: US 6,319,923 B1
(45) Date of Patent: *Nov. 20, 2001

(54) METHOD OF TREATING A TUMOR

(75) Inventors: Daniel L. Dexter, Holcombe, WI (US); Paul E. Juniewicz, West Chester; James B. Rake, Glenmoore, both of PA (US); Daniel D. Von Hoff, San Antonio, TX (US)

(73) Assignee: Sanofi-Synthelabo Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/505,043

(22) Filed: Feb. 16, 2000

Related U.S. Application Data

(60) Division of application No. 09/031,692, filed on Feb. 27, 1998, which is a continuation-in-part of application No. 08/814,769, filed on Mar. 7, 1997, now abandoned.

(51) Int. Cl.[7] .................. A61K 31/53; A61K 31/335; A61K 31/28; A61K 33/24
(52) U.S. Cl. .................. 514/243; 514/449; 514/492; 424/649
(58) Field of Search ............................ 514/243, 449, 514/492; 424/649

(56) References Cited

U.S. PATENT DOCUMENTS 5,484,612 * 1/1996 Brown .................................. 424/649
6,063,780 * 5/2000 Dexter et al. ........................ 514/243

OTHER PUBLICATIONS

Holden et al., J. National Cancer Inst., vol. 84, No. 3, Feb. 5, 1992.

Gale et al., Cancer, vol. 41, 1230–1234, 1978.

The Merck Index, 11th Edition, Merck & Co., Inc., Rahway, N.J. (1989), p. 1435.

Beale et al., Expert Opin. Invest. Drugs (1996), 5(6), pp. 681–693.

* cited by examiner

Primary Examiner—Jerome D. Goldberg
(74) Attorney, Agent, or Firm—Michael D. Alexander; Paul E. Dupont

(57) ABSTRACT

In accordance with the present invention there is provided a method of treating a mammal having a solid tumor, the method comprising:
a) administering to the mammal an effective amount of 3-ainino-1,2,4-benzotriazine 1,4-dioxide;
b) administering to the mammal an effective amount of paclitaxel; and
c) administering to the mammal an effective amount of a platinum complex. The method provides unexpected synergistic efficacy. The invention further provides a kit for treatment of a mammalian tumor comprising 3-amino-1, 2,-benzotriazine 1,4-dioxide, paclitaxel and a platinum complex.

7 Claims, 2 Drawing Sheets

METHOD OF TREATING A TUMOR

CROSS-REFERENCE TO RELATED APPLICATION

This application is a divisional of prior application Ser. No.09/031,692, filed Feb. 27, 1998, which in turn is a continuation-in-part of our prior application Ser. No. 08/814,769, filed Mar. 7, 1997 now abandoned.

FIELD OF THE INVENTION

The present invention relates to the field of treatments for cancer tumors. More specifically, the present invention relates to treatment of cancer tumors with tirapazamine, paclitaxel and a platinum complex.

BACKGROUND OF THE INVENTION

Tirapazamine is a bioreductive agent that preferentially kills hypoxic cells. Tirapazamine, i.e., 3-amino-1,2,4-benzotriazine 1,4-dioxide (SR-4233) has the structural formula

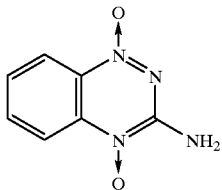

When given as multiple injections in conjunction with fractionated irradiation, tirapazamine kills hypoxic cells, increases tumor cell kill while sparing normal tissue in mouse SCCVII and other tumors as reported by: Brown, J. M., Potentiation by the hypoxic cytotoxin SR 4233 of cell killing produced by fractionated irradiation of mouse tumors, Cancer Res. 50:7745–7749 (1990) and Brown, J. M. et al, SR 4233: A tumor specific radiosensitizer active in fractionated radiation regimens, *Radiother, and Oncol.*, 20:151–156 (1991). Brown has considered that tumor hypoxia may actually be of a therapeutic advantage when combining a hypoxic cytotoxin such as tirapazamine with fractionated irradiation: Brown, J. M. et al., Tumor hypoxia: the picture has changed in the 1990s, *Int. J. Radiat. Biol.*, 65:95–102(1994); and Brown, J. M. et al, Therapeutic advantage of hypoxic cells in tumors: a theoretical study, *J. Nat Can. Inst.*, 83:178–185 (1991).

International Application No. PCT/US89/01037 discloses 1,2,4-benzotriazine oxides as radiosensitizers and selective cytotoxic agents. Related patents include: U.S. Pat. No. 5,175,287 which discloses the use of 1,2,4-benzotriazine oxides in conjunction with radiation for treatment of tumors. The 1,2,4-benzotriazine oxides sensitize the tumor cells to radiation and make them more amenable to this treatment modality. U.S. Pat. Nos. 3,868,372 and 4,001,410 which disclose the preparation of 1,2,4-benzotriazine oxides; and U.S. Pat. No. Nos. 3,991,189 and 3,957,799 which disclose derivatives of 1,2,4benzotriazine oxides.

Paclitaxel is a natural product with antitumor activity. The chemical name for paclitaxel is 5β,20-Epoxy-1,2α,4,7β,10β,13α-hexahydroxytax-11-en-9-one 4,10-diacetate 2-benzoate 13-ester with (2R, 3S)-N-benzoyl-3-phenylisoserine. Paclitaxel has the following structural formula:

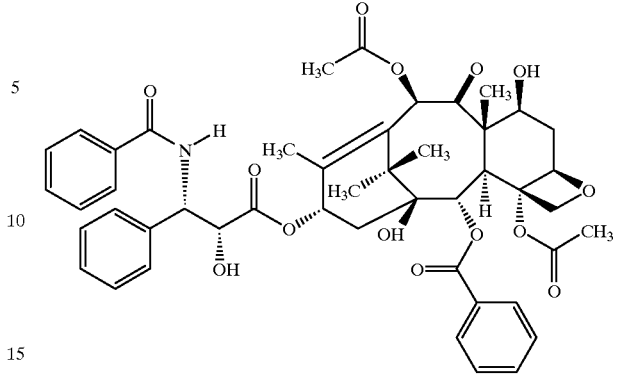

Paclitaxel is a white to off-white crystalline powder with the empirical formula $C_{47}H_{51}NO_{14}$ and a molecular weight of 853.9. It is highly lipophilic, insoluble in water, and melts at around 216–217° C.

Paclitaxel is an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of inicrotubules throughout the cell cycle and multiple asters of microtubules during mitosis.

Cisplatin is a platinum coordination complex that is used as a cancer chemotherapeutic agent. Cisplatin, i.e., cis-diamminedicbloroplatinum, has a central atom of platinum surrounded by two chloride atoms and two ammonia molecules in the cis position and the structural formula:

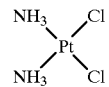

It is a white powder (m.p. ~207° C.) with the molecular formula $PtCl_2H_6N_2$ and a molecular weight of 300.1. It is soluble in water or saline at 1 mg/mL and in dimethylformamide at 24 mg/mL. Due to its chemical structure, the chlorine atoms of cisplatin are more subject to chemical displacement reactions by nucleophiles, such as water or sulfhydryl groups, than to enzyme catalyzed metabolism.

Carboplatin is a platinum coordination compound that is used as a cancer chemotherapeutic agent. The chemical name for carboplatin is platinum, diammine [1,1cyclobutane-dicarboxylato(2)-0,0',] (SPA-4-2). Carboplatin has the following structural formula:

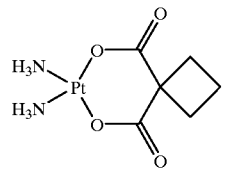

Carboplatin is a crystalline powder with the molecular formula $C_6H_{12}N_2O_4Pt$ and a molecular weight of371.25. It is soluble in water at a rate of approximately 14 mg/mL, and the pH of a 1% solution is 5–7. It is virtually insoluble in ethanol, acetone and dimethylacetamide. Carboplatin, like cisplatin, produces predominantly interstrand DNA cross-links rather than DNA-protein cross-links. This effect is apparently cell-cycle nonspecific. The aquation of carboplatin which is thought to produce the active species, occurs at a slower rate than in the case of cisplatin. Despite this difference, it appears that both carboplatin and cisplatin induce equal numbers of drug-DNA cross-links, causing equivalent lesions and biological effects. The differences in potencies for carboplatin and cisplatin appear to be directly related to the difference in aquation rates.

Another platinum complex which has shown clinical promise is oxaliplatin. Oxaliplatin, i.e., cis-oxalato(trans-1-1,2-cyclohexanediamine) platinum (II) having the structure

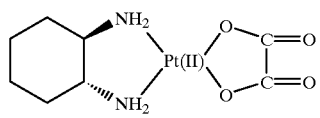

is described in U.S. Pat. No. 4,169,846. Related patents include: U.S. Pat. No. 5,290,961; U.S. Pat. 5,298,642; U.S. Pat. No. 5,338,874; U.S. Pat. No. 5,420,319 and PCT/IB100614.

Holden et al (1992) "Enhancement of Alkylating Agent Activity by SR-4233 in the FSaIIC Murine Fibrosarcoma" JNCI 84: 187–193 discloses the use of SR-4233, also known as tirapazamine, in combination with an antitumor allating agent. The four antitumor alkylating agents, cisplatin, cyclophosphamide, carmustine and melphalan, were each tested to examine the ability of tirapazamine to overcome the resistance of hypoxic tumor cells to antitumor alkylating agents. Tirapazamine was tested alone and in combination with varying amounts of each of the antitumor alkylating agents. When SR4233 was administered just before single-dose treatment with cyclophosphamide, caimustine or melphalan marked dose enhancement leading to synergistic cytotoxic effects on tumor cells was observed. When SR4233 was administered just prior to single-dose treatment with cisplatin, however, the dose enhancement lead to an additive effect, except at the highest dose level of cisplatin.

Brown, U.S. Pat. No. 5,484,612 discloses the treatment of cancer tumors with combinations of chemotherapy agents and 1,2,4-benzotriazine oxides.

SUMMARY OF THE INVENTION

We have discovered that the triple combination of tirapazamine, paclitaxel and a platinum complex provides unexpectedly greater than additive, i.e., synergistic, efficacy when administered in the treatment of mammalian tumors compared to double combinations of these anticancer agents.

The present invention provides a method of treating a mammal having a solid tumor. The method comprises:
 a) administering to the mammal an effective amount of 3-anmino-1,2,4-benzotriazine 1,4-dioxide;
 b) administering to the mammal an effective amount of paclitaxel; and
 c) administering to the mammal an effective amount of a platinum complex.

The present invention further provides a kit for treatment of mammalian tumors comprising:
 3-amino-1,2,4-benzotriazine 1,4-dioxide;
 paclitaxel; and
 a platinum complex.

DESCRIPTION OF THE PREFERRED EMBODIMENTS

Figure 1:
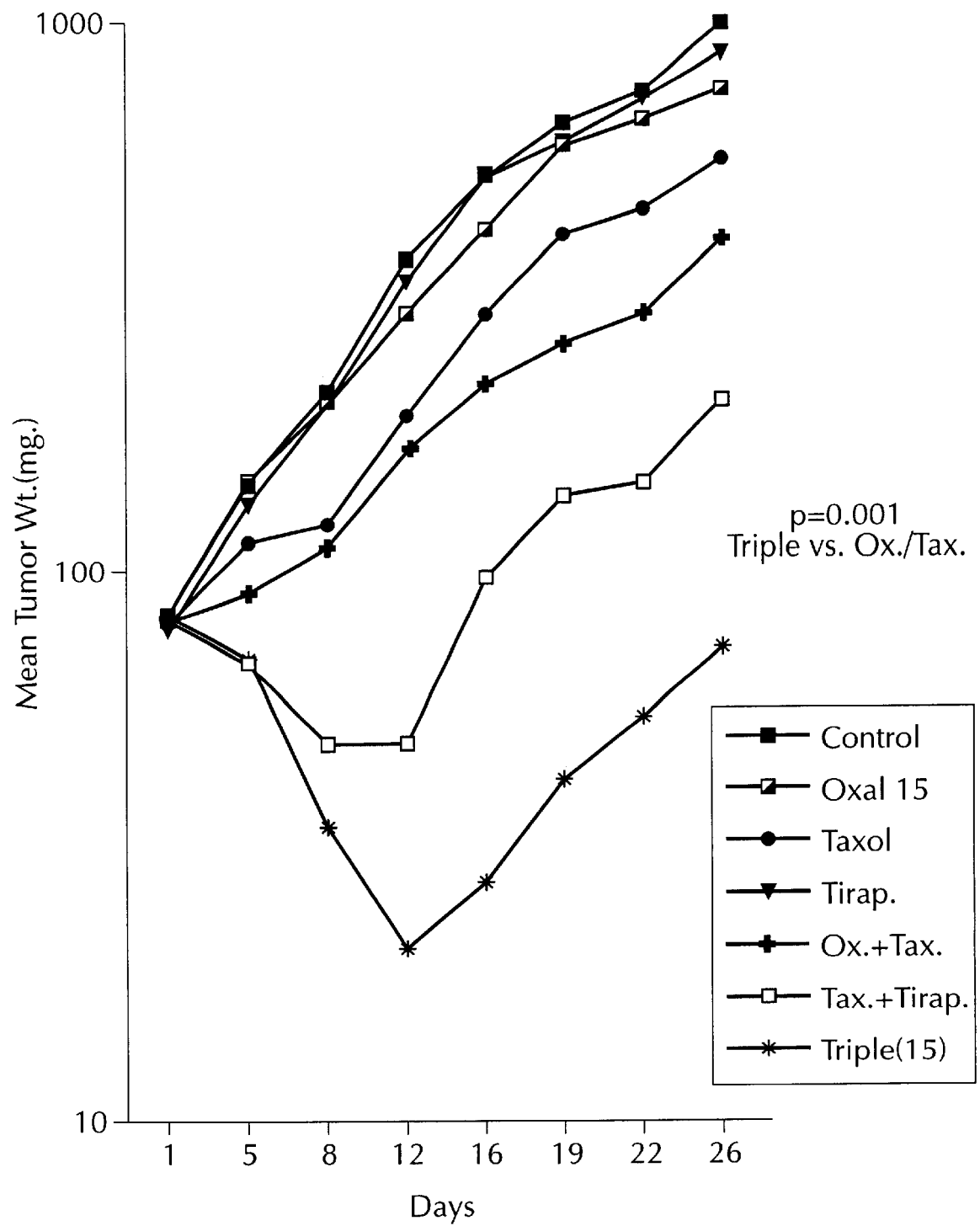
FIGS. 1 and 2 illustrate mean tumor weight versus time for methods of treatment employing tirapazamine, paclitaxel and a platinum complex as single agents and in combination.

The invention is hereinafter described particularly with regard to preferred embodiments featuring tirapazamine and paclitaxel. In addition, it is contemplated that the invention can be practiced in conjunction with analogs of tirapazamine and analogs of paclitaxel.

The anticancer agents useful in the practice of this invention, e.g., tirapazamine, paclitaxel and the platinum complex, are known compounds and/or can be prepared by techniques known in the art.

In addition to the platinum complexes described above, it is believed that the invention can be practiced with other platinum complexes. Suitable platinum complexes are described in U.S. Pat. No. 5,562,925.

The anticancer agents useful in the practice of this invention are administered to the mammal by known conventional routes appropriate for the particular anticancer agent. The anticancer agents described herein can be administered by the same route, or by different routes. For example, the anticancer agents may be administered to patients orally or parenterally (intravenously, subcutaneously, intramuscularly, intraspinally, intraperitoneally, and the like).

When administered parenterally the compounds will normally be formulated in a unit dosage injectable form (solution, suspension, emulsion) with a pharmaceutically acceptable vehicle. Such vehicles are typically nontoxic and non-therapeutic. Examples of such vehicles are water, aqueous vehicles such as saline, Ringer's solution, dextrose solution, and Hank's solution and non-aqueous vehicles such as fixed oils (e.g., corn, cottonseed, peanut and sesame), ethyl oleate, and isopropyl myristate. Sterile saline is a preferred vehicle. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a table, capsule, suppository, or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, methylcellulose, polyoxyethylene, sorbitan monolaurate, methyl hydroxybenzoate, propyl hydroxybenzoate, talc and magnesium stearate. In preferred embodiments, the anticancer agents are administered intravenously.

The anticancer agents useful herein can be administered simultaneously or sequentially. It is believed that the enhanced efficacy observed does not depend upon the timing of administration. In preferred embodiments, tirapazamine is administered to the mammal from about one-half hour to about 24 hours prior to administration of the paclitaxel and platinum a complex.

The anticancer agents are administered to the mammal in amounts effective to treat susceptible tumors. Such amounts are well known in the art and can be ascertained by reference to, in the case of paclitaxel, cisplatin and carboplatin, to product literature furnished by the supplier. Additionally, the amounts can be ascertained by reference to the scientific literature.

For example, tirapazamine is administered to the mammal in amounts effective to kill or produce cytotoxic effects upon hypoxic tumor cells. The amount of tirapazamine administered will depend on such factors as the type of cancer tumor, the age and health of the mammal, the maximum tolerated and/or lethal dosage and the interaction with the other anticancer chemotherapy agents. In preferred embodiments of the invention, tirapazamine is administered in amounts of from about 10 mg/m$^2$ to about 450 mg/m$^2$; more preferably from about 20 mg/m$^2$ to about 350 mg/m$^2$; most preferably from about 30 mg/m$^2$ to about 250 mg/m$^2$. Preferred dosing regimens for tirapazamine include those described in International Application No. PCTIUS89/04112.

In preferred embodiments, the taxane derivative can be administered in amounts of from about 30 mg/m$^2$ to 300 mg/m$^2$; more preferably from 50 mg/m$^2$ to 250 mg/m$^2$; most preferably from 100 mg/m$^2$ to 200 mg/m$^2$. Paclitaxel is available under the tradename TAXOL in 30 mg (5 mL) single-dose vials. Each mL of sterile nonpyrogenic solution contains 6 mg paclitaxel, 527 mg of Cremophor ® EL (polyethoxylated castor oil) and 49.7% (v/v) dehydrated alcohol, USP. This nonaqueous solution is intended for dilution with a suitable parenteral fluid prior to intravenous infusion. Paclitaxel can be diluted with 0.9% Sodium Chloride Injection, USP, 5% Dextrose Injection, USP, 5% Dextrose and 0.9%/Sodium Chloride Injection, USP, or 5% Dextrose in Ringers' Injection to a final concentration of 0.3–1.2 mg/mL. Preferred dosing regiments for paclitaxel include those described in the 1996 Edition of the Physicians Desk Reference.

In preferred embodiments, the platinum complex can be administered in amounts of from about 10 mg/m$^2$ to about 250 mg/m$^2$; more preferably from about 20 mg/m$^2$ to 200 mg/m$^2$; most preferably from about 30 mg/m$^2$ to 180 mg/m$^2$. The oxaliplatin preferably is presented in the form of a freeze-dried powder for infusion in vials containing 50 mg or 100 mg of oxaliplatin and 450 mg or 900 mg of lactose monohydrate. The freeze-dried powder can be reconstituted by adding 10 to 20 ml (for the 50 mg vial) or 20 to 40 ml (for the 100 mg vial) of water for injection or 5% glucose solution and then by diluting in an infusion solution of 250 ml or 500 ml of 5% glucose. Reconstitution or final dilution preferably should not be performed with a sodium chloride solution. The oxaliplatin can be infused intravenously, preferably over a period of up to 4 hours. Currently preferred dosing regiments for oxaliplatin include administration of repeated dosages of oxaliplatin in cycles of 1, 3 and 5 days, the number of cycles varying from 1 to 6. Preferred dosing regiments for carboplatin and cisplatin include those described in the 1996 Edition of the Physicians Desk Reference.

Methods and Results

MV-522 Human Lung Tumor Xenograft

Nude mice weighing approximately 20 g were implanted s.c. by trocar with fragments of MV-522 human lung carcinomas harvested from s.c. growing tumors in nude mice hosts. When tumors were approximately 5 mm×5 mm in size (usually ten days after inoculation), the animals were pair-matched into treatment and control groups. Each group contained 8 tumored nice, each of which was ear-tagged and followed individually throughout the experiment. The administration of drugs or vehicle began the day the animals were pair-matched (Day 1). The doses, route of drug administration and schedule were selected as appropriate for the study. If the MMD dose of an agent was not known, it was determined in an initial dosing experiment in non-tumored mice.

Mice were weighed twice weekly, and tumor measurements were taken by calipers twice weekly, starting on Day 1. These tumor measurements were converted to mg tumor weight by a well-known formula, $L^2 \times W/2$. The experiment was terminated when control tumors reached a size of approximately 1 gram. Upon termination, all mice were weighed, sacrificed, and their tumors excised. Tumors were weighed, and the mean tumor weight per group was calculated. In these models, the mean treated tumor weightlmean control tumor weight×100% (T/C) is subtracted from 100% to give the tumor growth inhibition (TGI) for each group.

Some drugs caused tumor shrinkage in the MV-522 human lung tumor xenograft model. With these agents, the final weight of a given tumor was subtracted from its own weight at the start of treatment on Day 1. This difference divided by the initial tumor weight is the % shrinkage. A mean % tumor shrinkage can be calculated from data from the mice in a group that experienced tumor regressions. If the MV-522 tumor completely disappeared in a mouse, this was considered a complete regression or complete tumor shrinkage. If desired, mice with partial or total tumor regressions can be kept alive past the termination date to see whether they live or become long term, tumor-free survivors.

The study of the comparison of the carboplatin-paclitaxel-tirapazamine regimen with the oxaliplatin-paclitaxel-tirapazamine regimen was conducted in one large, controlled experiment involving two hundred mice. The activities of each of the three drugs as single agents was determined, and the efficacies of various three-way (triple) combinations of the agents were also evaluated. A number of mice in this study experienced tumor shrinkage at the termination of the experiment. In this report, to facilitate the description of the results, any lung tumor shrinkage between 1% and 99% in an animal will be noted as a partial response (PR), and any mouse with complete shrinkage (disappearance) of its neoplasm will be considered as a complete response (CR). The efficacy of treatment in the remainder of the mice will be presented as tumor growth inhibition values.

RESULTS

EXAMPLE 1

Oxaliplatin-Paclitaxel-Tirapazamine Regimen

High and low doses of oxaliplatin, paclitaxel and tirapazamine were combined versus the MV-522 tumor in all possible triple combinations of the three drugs. Every triple combination was active. Tumor shrinkage occurred at the end of the study in seven of the eight combination groups; only the triple combination of the low doses of all three agents failed to produce tumor shrinkage. Seven cases of complete tumor shrinkage (CRs) were recorded among groups in this regimen, and eight cases of partial tumor shrinkage (PRs) were noted. Three CRs were obtained in the group of eight mice treated with low dose oxaliplatin—high dose paclitaxel,—high dose tirapazamine, the highest number of CRs obtained in any group in the entire study.

This regimen was very well-tolerated by the mice. Weight losses on Day 6 (the day of peak weight loss) ranged form 3.2% to 10.7% among the eight groups, and no toxic deaths were recorded in this cohort of 64 mice.

EXAMPLE 2

Caiboplatin-Paclitaxel-Tirapazamine Regimen

High and low doses of carboplatin, paclitaxel and tirapazamine were combined in the MV-522 experiment using all possible triple combinations of the three agents. As with the oxaliplatin-containing regimen, all triple combinations of the carboplatin-regimen were active. Two cases of complete tumor shrinkage (CRs) and six instance of partial tumor shrinkage (PRs) were recorded with this regimen at the end of the study. Four of the eight tumor shrinkage cases were obtained in the group study. Four of the eight tumor shrinkage cases were obtained in the group receiving high dose carboplatin—high dose paclitaxel4ow dose tirapazamine.

The carboplatin—containing combinations were quire well-tolerated by the 64 animals receiving this regimen. Weight changes ranged from a weight gain of 1.7% to a weight loss of 14.9% among the eight groups. One toxic death occurred with this regimen (high dose carboplatin—lower dose paclitaxel—high dose tirapazamine).

The results described above were confirmed in the following study.

Nude mice weighing approximately 20 g were implanted s.c. by trocar with fragments of MV-522 human lung carcinomas harvested from s.c. growing tumors in nude mice hosts. When tumors were approximately 5 mm×5 mm in size (usually ten days after inoculation), the animals were pair-matched into treatment and control groups. Each group contained 8 tumored mice, each of which was ear-tagged and followed individually throughout the experiment. Tirapazamine was administered three hours prior to oxaliplatin, carboplatin and paclitaxel. The route and schedule for all drugs was i.p., qdxi.

Mice were weighed twice weekly, and tumor measurements were taken by calipers twice weekly, starting on Day 1. These tumor measurements were converted to mg tumor weight by a well-known formula, $L \times W^2/2$. The experiment was terminated when control tumors reached a size of 1 gram. Upon termination, all mice were weighed, sacrificed, and their tumors excised. Tumors were weighed, and the mean tumor weight per group was calculated. In these models, the mean treated tumor weight/mean control tumor weight×100% (TIC) is subtracted from 100% to give the tumor growth inhibition (TGI) for each group.

Some drug combinations caused tumor shrinkage in the MV-522 human lung tumor xenograft model. With these agents, the final weight of a given tumor was subtracted from its own weight at the start of treatment on Day 1. This difference divided by the initial tumor weight is the % shrinkage. A mean % tumor shrinkage can be calculated from data from the mice in a group that experienced tumor regressions. If the MV-522 tumor completely disappeared in a mouse, this was considered a complete regression or complete tumor shrinkage.

TABLE 1

Carboplatin, Paclitaxel and Tirapazamine vs MV-522 Human Lung Tumor Xerograft

| Group | n | Dose & Route | Schedule | Weight Change (Day 6) | Final Tumor Wt. (Mean ± SEM) | % Tumor Growth Inhibition | Mice with partial Shrinkage | Mean % Tumor Shrinkage | Mice with Complete Shrinkage | # of Toxic Deaths |
|---|---|---|---|---|---|---|---|---|---|---|
| Control | (8) | Saline/i.p. | qdx1 | +1.5% | 881.9 ± 93.1 | 0.0 | 0 | — | 0 | 0 |
| Carboplatin | (8) | 100 mg/kg/i.p. | qdx1 | −1.5% | 556.5 ± 129.8 | 39.7 | 0 | — | 0 | 0 |
| Carboplatin | (8) | 50 mg/kg/i.p. | qdx1 | −1.7% | 698.1 ± 160.5 | 22.5 | 0 | — | 0 | 0 |
| Paclitaxel | (8) | 20 mg/kg/i.p. | qdx1 | +0.4% | 552.9 ± 68.6 | 40.2 | 0 | — | 0 | 1 |
| Tirapazamine | (8) | 70 mg/kg/i.p. | qdx1 | −1.7% | 835.3 ± 111.2 | 5.7 | 0 | — | 0 | 0 |
| Paclitaxel + Tirapazamine | (8) | 20 mg/kg/i.p. 70 mg/kg/i.p. | qdx1 | +2.7% | 284.0 ± 51.8 | 73.0 | 0 | — | 0 | 0 |
| Paclitaxel + Carboplatin | (8) | 20 mg/kg/i.p. 100 mg/kg/i.p. | qdx1 | −1.3% | 241.4 ± 70.3 | 68.8 | 2 | 53.0 | 0 | 0 |
| Paclitaxel + Carboplatin | (8) | 20 mg/kg/i.p. 50 mg/kg/i.p. | qdx1 | +1.7% | 474.0 ± 93.5 | 49.8 | 0 | — | 0 | 0 |
| Tirapazamine + Carboplatin | (8) | 70 mg/kg/i.p. 100 mg/kg/i.p. | qdx1 | −3.8% | 600.5 ± 85.6 | 34.4 | 0 | — | 0 | 0 |
| Tirapazamine + Carboplatin | (8) | 70 mg/kg/i.p. 50 mg/kg/i.p. | qdx1 | −4.2% | 549.8 ± 95.8 | 40.3 | 0 | — | 0 | 0 |
| Carboplatin + Paclitaxel + Tirapazamine | (8) | 100 mg/kg/i.p. 20 mg/kg/i.p. 70 mg/kg/i.p. | qdx1 | −2.4% | 50.4 ± 30.9 | 85.9 | 2 | 77.3 | 4 | 0 |
| Carboplatin + Paclitaxel + Tirapazamine | (8) | 50 mg/kg/i.p. 20 mg/kg/i.p. 70 mg/kg/i.p. | qdx1 | +3.4% | 58.4 ± 39.8 | 61.2 | 4 | 54.9 | 3 | 0 |

RESULTS

EXAMPLE 3

Carbbplatin—Tirapazamine—Pachltaxel

The results of the large experiment in which carboplatin, paclitaxel and tirapazamine were tested as single agents in a two- and three-way combinations versus the MV-522 tumor are presented in Table 1 and FIG. 1. Paclitaxel and tirapazamine were administered i.p. as a single bolus at doses of 20 mg/kg (⅔ MTD) and 70 mg/kg (MTD) respectively. Carboplatin was given as a single i.p. bolus at doses of 100 mg/kg (MTD) or 50 mg/kg (½ MTD). Paclitaxel and carboplatin (100 mg/kg) given as single agents each caused a small tumor growth inhibition (TGI) of approximately 40%. Tirapazamine was not active as a single agent. The paclitaxel-tirapazamine combination demonstrated good activity, causing a TGI=73%. The paclitaxel-high dose carboplatin regimen was even more effective, producing a mean 53% tumor shrinkage in two mice, and a 68.8% TGI in the remaining six animals in this group. The tirapazamine-carboplatin combinations were not any more effective than carboplatin alone.

Triple combinations of the three drugs were highly efficacious against the MV-522 carcinoma. The triple drug combination with high dose carboplatin caused a mean 77.3% tumor shrinkage in two mice, a complete tumor regression in four mice, and a TGI=85.9% in the other two animals in this group. The triple drug regiment with low dose carboplatin was also highly active, producing three cases of complete tumor shrinkage, four cases with a mean 54.7% tumor shrinkage, and a TGI of 61.2% in one mouse.

A statistical analysis was performed on these data (see Table 2) using the pooled variances t test. There was a strong trend for the single agent carboplatin 100 mg/kg dose group to attain statistical significance versus the control group (p=0.075). Paclitaxel as a single agent did produce a statistically significant antitumor effect compared to the control group (p=0.024). A high degree of statistical significance was achieved with both the paclitaxel-tirapazamine and paclitaxel-carboplatin (100 mg/kg) combinations compared to paclitaxel alone (p=0.013 in each instance). The triple combination with carboplatin given at 100 mg/kg was more efficacious than the paclitaxel-carboplatin (100 mg/kg) double combination, with a p value of 0.059. This triple combination versus the paclitaxel-tirapazamine double combination was highly statistically significantly more active, with a p value of 0.007 determined for the comparison of these two groups.

TABLE 2

STATISTICAL ANALYSIS — CARBOPLATIN ARM

| Comparison | p Value |
| --- | --- |
| Carboplatin (100) vs Control | 0.075 |
| Paclitaxel vs Control | 0.024 |
| Paclitaxel + Tirapazamine vs Paclitaxel | 0.013 |
| Paclitaxel + Carboplatin (100) vs Paclitaxel | 0.013 |
| Paclitaxel + Carboplatin (100) vs Carboplatin (100) | 0.064 |
| Paclitaxel + Tirapazamine + Carboplatin (100) vs Paclitaxel + Carboplatin (100) | 0.059 |
| Paclitaxel + Tirapazamine + Carboplatin (100) vs Paclitaxel + Tirapazamine | 0.007 |

A very important finding from this experiment was that all regimens were quite well-tolerated (Table 1). No group lost more than 4.2% body weight on Day 6, and there way only one toxic death recorded among the 96 mice in the experiment (in the single agent paclitaxel group). Thus, triple combinations of these three agents were as well tolerated as the drugs given alone.

The triple combination of paclitaxel and tirapazamine with carboplatin given at doses of 100 mg/kg or 50 mg/kg produced complete or partial tumor shrinkage in six and seven mice respectively out of sixteen treated animals. The oxaliplatin-paclitaxel-tirapazamine regiments tested in an independent experiments were also highly effective. The results were highly statistically significant.

EXAMPLE 4

Oxaliplatin-Tirapazamine-Paclitaxel

Figure 2:
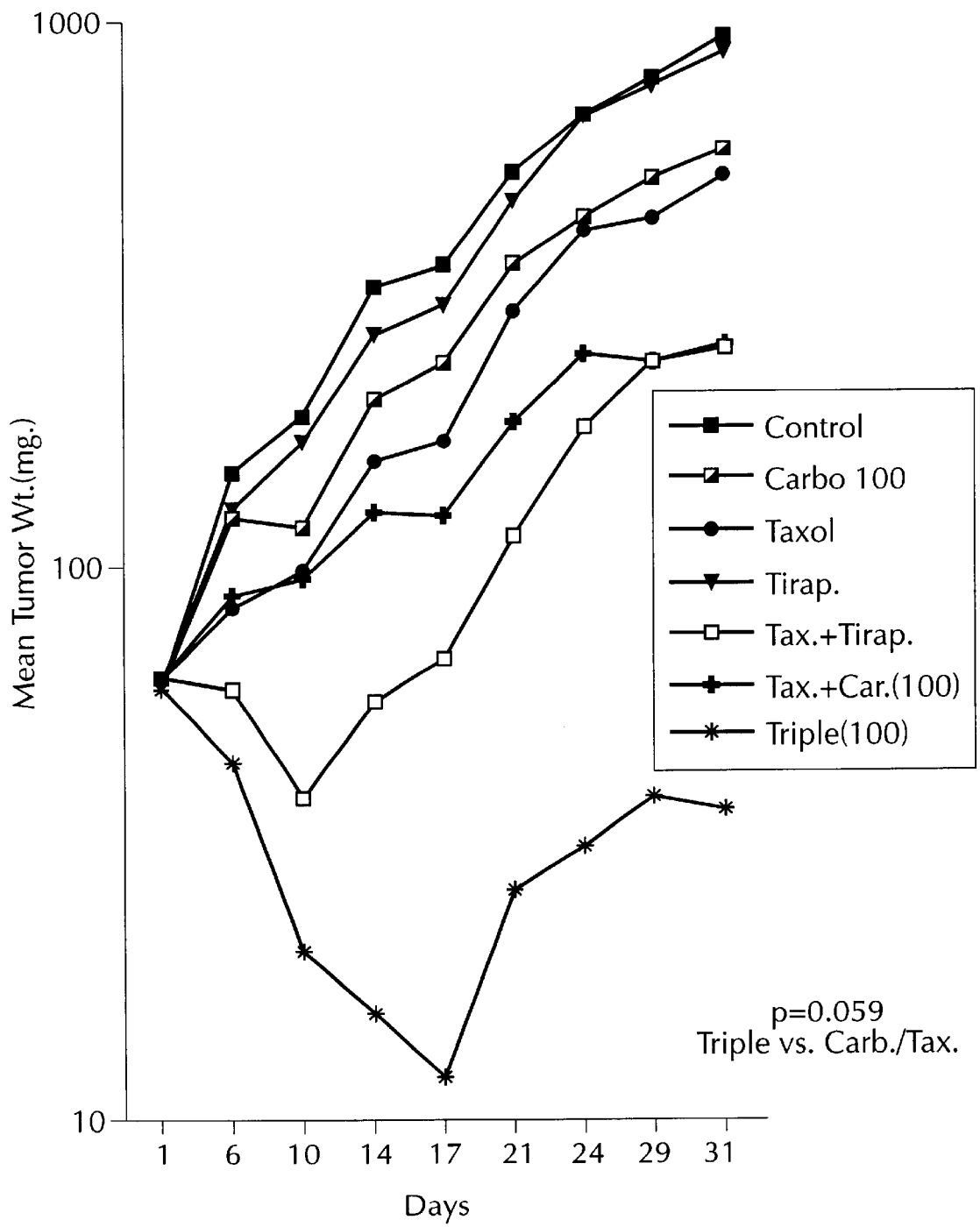

The results of the initial experiment with oxaliplatin, paclitaxel and tirapazamine administered as single agents or in various two- and three-way combinations versus the MV-522 human lung carcinoma xenograft are shown in Table 3 and FIG. 2. Paclitaxel and tirapazamine were given at doses of 20 mg/kg and 70 mg/kg respectively (i.p.; qdx1). Oxaliplatin was given at 15 mg/kg BTD). Oxaliplatin and tirapazamine given as single agents were not active in this test. Paclitaxel alone produced a marginal TGI=30.9%. the paclitaxel-oxaliplatin combination was more efficacious than paclitaxel alone (TGI=55.4%). The paclitaxel-tirapazamine combination was highly effective, producing a mean 29.2% tumor shrinkage in three mice and a TGI=73.1% in the other five animals in this group. The triple combination gave unexpectedly impressive results, causing a mean 72.4% tumor shrinkage in four mice and TGI=87.0% in the other four animals in this treatment group.

The pooled variances t test was also performed on the data from the repeat experiment (Table 4). The efficacy difference between paclitaxel plus oxaliplatin versus paclitaxel alone demonstrated borderline statistical significance (p=0.076). In contrast, the difference between the paclitaxel-tirapazamine combination treatment group versus the paclitaxel alone group was highly significant (p=0.005). The triple combination results compared to the effect caused by the paclitaxel-oxaliplatin combination was extremely significant (p=0.001). There was no statistically significant difference between the results achieved with the triple combination compared to the paclitaxel-tirapazamine combination (p=0.401).

As was the case with the first experiment in this study, all groups on the repeat experiment tolerated all regiments very well. No toxic deaths occurred in this experiment, and body weight loss was generally minimal (Table 4).

TABLE 3

Oxaliplatin, Paclitaxel and Tirapazamine vs MV-522 Human Lung Tumor Xerograft

| Group | n | Dose & Route | Schedule | Weight Change (Day 6) | Actual Tumor Wt. (Mean ± SEM) | % Tumor Growth Inhibition | Mice with partial Shrinkage | Mean % Tumor Shrinkage | Mice with Complete Shrinkage | # of Toxic Deaths |
| --- | --- | --- | --- | --- | --- | --- | --- | --- | --- | --- |
| Control | (8) | Saline/i.p. | qdx1 | +2.2% | 791.4 ± 94.0 | 0.0 | 0 | — | 0 | 0 |
| Oxaliplatin | (8) | 15 mg/kg/i.p. | qdx1 | +5.2% | 731.5 ± 62.6 | 8.2 | 0 | — | 0 | 0 |
| Paclitaxel | (8) | 20 mg/kg/i.p. | qdx1 | +0.9% | 570.5 ± 69.3 | 30.9 | 0 | — | 0 | 1 |
| Tirapazamine | (8) | 70 mg/kg/i.p. | qdx1 | -6.9% | 769.1 ± 73.0 | 2.5 | 0 | — | 0 | 0 |
| Paclitaxel + Oxaliplatin | (8) | 20 mg/kg/i.p. 15 mg/kg/i.p. | qdx1 | +1.2% | 395.3 ± 43.8 | 55.4 | 0 | — | 0 | 0 |
| Tirapazamine + Oxaliplatin | (8) | 70 mg/kg/i.p. 15 mg/kg/i.p. | qdx1 | -9.5% | 615.9 ± 68.2 | 24.2 | 0 | — | 0 | 0 |
| Paclitaxel + | (8) | 20 mg/kg/i.p. | qdx1 | -15.0% | 189.9 ± 75.2 | 73.1 | 3 | 29.2 | 0 | 0 |

TABLE 3-continued

Oxaliplatin, Paclitaxel and Tirapazamine vs MV-522 Human Lung Tumor Xerograft

| Group | n | Dose & Route | Schedule | Weight Change (Day 6) | Actual Tumor Wt. (Mean ± SEM) | % Tumor Growth Inhibition | Mice with partial Shrinkage | Mean % Tumor Shrinkage | Mice with Complete Shrinkage | # of Toxic Deaths |
|---|---|---|---|---|---|---|---|---|---|---|
| Tirapazamine Oxaliplatin + Paclitaxel + Tirapazamine | (8) | 70 mg/kg/i.p. 15 mg/kg/i.p. 20 mg/kg/i.p. 70 mg/kg/i.p. | qdx1 | −7.9% | 107.9 ± 39.0 | 87.0 | 4 | 72.4 | 0 | 0 |

TABLE 4

STATISTICAL ANALYSIS — OXALIPLATIN ARM

| Comparison | p Value |
|---|---|
| Oxaliplatin vs Control | 0.643 |
| Paclitaxel vs Control | 0.113 |
| Paclitaxel + Tirapazamine vs Paclitaxel | 0.005 |
| Paclitaxel + Oxaliplatin vs Paclitaxel | 0.076 |
| Paclitaxel + Tirapazamine + Oxaliplatin vs Paclitaxel + Tirapazamine | 0.401 |
| Paclitaxel + Tirapazamine + Oxaliplatin vs Paclitaxel + Oxaliplatin | 0.001 |

While applicants do not wish to be bound by theoretical mechanisms, it is noted that the scientific literature proposes different molecular mechanisms of actions for tirapazamine, paclitaxel and platinum complexes. The different mechanisms of action may in part lead to the synergistic efficacy observed. Therefore it is contemplated that analogs of tirapazamine and analogs of paclitaxel may also provide the enhanced efficacy observed herein. Suitable analogs of tirapazamine can be selected from those described in International Application PCT/US89/04112. Suitable analogs of paclitaxel include taxane derivatives such as docetaxel and other analogs described in U.S. Pat. No. 4,814,470 and U.S. Pat. No. 5,403,858.

Having described the invention with reference to its preferred embodiments, it is to be understood that modifications within the scope of the invention will be apparent to those skilled in the art.

What is claimed is:

1. A method of treating a mammal having a solid tumor, said method comprising administering to said mammal a synergistically effective amount of 3-amino-1,2,4-benzotriazine 1,4-dioxide;

paclitaxel; and a platinum complex selected from the group consisting of cisplatin and carboplatin.

2. The method of claim 1 wherein said platinum complex is cisplatin.

3. The method of claim 1 wherein said platinum complex is carboplatin.

4. A kit for treatment of a mammalin tumor comprising a synergistically effective amount of 3-amino-1,2,4-benzotriazine 1,4-dioxide, paclitaxel and a platinum complex selected from the group consisting of oxaliplatin, cisplatin and carboplatin.

5. The kit of claim 4, wherein said platinum complex is cisplatin.

6. The kit of claim 4, wherein said platinum complex is carboplatin.

7. The kit of claim 4, wherein said platinum complex is obaliplatin.

* * * * *

UNITED STATES PATENT AND TRADEMARK OFFICE
CERTIFICATE OF CORRECTION

PATENT NO. : 6,319,923 B1
DATED : November 20, 2001
INVENTOR(S) : Dexter et al.

It is certified that error appears in the above-identified patent and that said Letters Patent is hereby corrected as shown below:

<u>Column 3,</u>
Line 25, "PCT/IB100614" should read -- PCT/IB/00614 --
Line 29, "in combination with an antitumor allating" should read -- in combination with an antitumor alkylating --
Line 37, "caimustine" should read -- carmustine --

<u>Column 4,</u>
Line 63, "platinum a complex" should read -- platinum complex --

<u>Column 5,</u>
Lines 16-17, "PCTIUS89/04112" should read -- PCT/US89/04112 --

<u>Column 6,</u>
Line 5, "MMD" should read -- MTD --
Line 16, "weightlmean" should read -- weight/mean --

<u>Column 7,</u>
Line 17, "paclitaxe14ow" should read -- paclitaxel-low --
Line 65, "qdxi" should read -- qdx1 --

<u>Column 8,</u>
Line 8, "(TIC)" should read -- (T/C) --
Line 53, "Carbbplatin–Tirapazamine–Pachltaxel" should read
-- – Carboplatin–Tirapazamine–Paclitaxel – --

UNITED STATES PATENT AND TRADEMARK OFFICE
CERTIFICATE OF CORRECTION

PATENT NO.   : 6,319,923 B1
DATED        : November 20, 2001
INVENTOR(S)  : Dexter et al.

It is certified that error appears in the above-identified patent and that said Letters Patent is hereby corrected as shown below:

Column 12,
Line 40, "obaliplatin" should read -- oxaliplatin --

Signed and Sealed this

Twenty-second Day of March, 2005

JON W. DUDAS
*Director of the United States Patent and Trademark Office*